(12) United States Patent
Shimada et al.

(10) Patent No.: US 9,335,388 B2
(45) Date of Patent: May 10, 2016

(54) REFERENCE MATERIAL FOR NMR, SAMPLE TUBE FOR NMR, CAPILLARY FOR NMR, AND METHOD FOR MEASURING NMR FOR A SAMPLE

(75) Inventors: Haruo Shimada, Kanagawa (JP); Keiko Ootake, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 981 days.

(21) Appl. No.: 13/520,420

(22) PCT Filed: Dec. 28, 2010

(86) PCT No.: PCT/JP2010/073732
§ 371 (c)(1),
(2), (4) Date: Jul. 3, 2012

(87) PCT Pub. No.: WO2011/083730
PCT Pub. Date: Jul. 14, 2011

(65) Prior Publication Data
US 2012/0313644 A1    Dec. 13, 2012

(30) Foreign Application Priority Data

Jan. 6, 2010  (JP) ................................. 2010-001200
Jan. 6, 2010  (JP) ................................. 2010-001201

(51) Int. Cl.
*G01V 3/00*     (2006.01)
*G01R 33/30*    (2006.01)
*G01R 33/46*    (2006.01)
*G01N 24/08*    (2006.01)

(52) U.S. Cl.
CPC ................ *G01R 33/30* (2013.01); *G01R 33/46* (2013.01); *G01N 24/08* (2013.01)

(58) Field of Classification Search
CPC ....................................................... G01R 33/30
USPC .................................................. 324/321, 318
See application file for complete search history.

(56) References Cited

U.S. PATENT DOCUMENTS 3,950,135 A    4/1976  Whitesides et al.
4,550,082 A    10/1985 Martin et al.
(Continued)

FOREIGN PATENT DOCUMENTS

EP      1331012 A1    7/2003
JP      58-154646     9/1983
(Continued)

OTHER PUBLICATIONS

Chinese Office Action dated Mar. 14, 2014.
(Continued)

*Primary Examiner* — Louis Arana
(74) *Attorney, Agent, or Firm* — IPUSA, PLLC

(57) ABSTRACT

Disclosed is a reference material for NMR, including a nitrogen-containing compound or oxygen-containing compound and a reagent for shifting a chemical shift for the nitrogen-containing compound or oxygen-containing compound. Disclosed is a sample tube for NMR, being obtainable by providing a reference material for NMR to a first tube closed at one end, providing a second tube closed at one end into the first tube, and fusing the other end of the first tube and the other end of the second tube and sealing a gap between the other end of the first tube and the other end of the second tube.

17 Claims, 6 Drawing Sheets

(56) References Cited

U.S. PATENT DOCUMENTS

| | | | |
|---|---|---|---|
| 5,122,472 A * | 6/1992 | Silks et al. | 436/173 |
| 2005/0191243 A1 | 9/2005 | Aime et al. | |
| 2008/0224703 A1 | 9/2008 | Molev et al. | |
| 2009/0234221 A1 | 9/2009 | Aime et al. | |

FOREIGN PATENT DOCUMENTS

| | | |
|---|---|---|
| JP | 60-171019 | 9/1985 |
| JP | 63-100031 | 5/1988 |
| JP | 01-302148 | 12/1989 |
| JP | 2004-122095 | 4/2004 |
| JP | 2004-286712 | 10/2004 |
| WO | WO 01 18534 A1 * | 3/2001 |

OTHER PUBLICATIONS

The extended European search report mailed Sep. 19, 2013.

Howarth O.W.: "Recording One-Dimensional High Resolution Spectra" In: Grant D.M., Harris R.K.: "Encyclopedia of Nuclear Magnetic Resonance", 1996, John Wiley & Sons, England ISBN: 0 471 93871 8 pp. 3967-3977.

Christophoridou Stella, et al., Detection and quantification of phenolic compounds in olive oil by high resolution 1H nuclear magnetic resonance spectroscopy, Analytica Chimica Acta, Jan. 30, 2009, Vo.633, No. 2, pp. 283-292.

International Search Report mailed on Mar. 29, 2011.

Taiwanese Office Action dated Aug. 28, 2015.

* cited by examiner

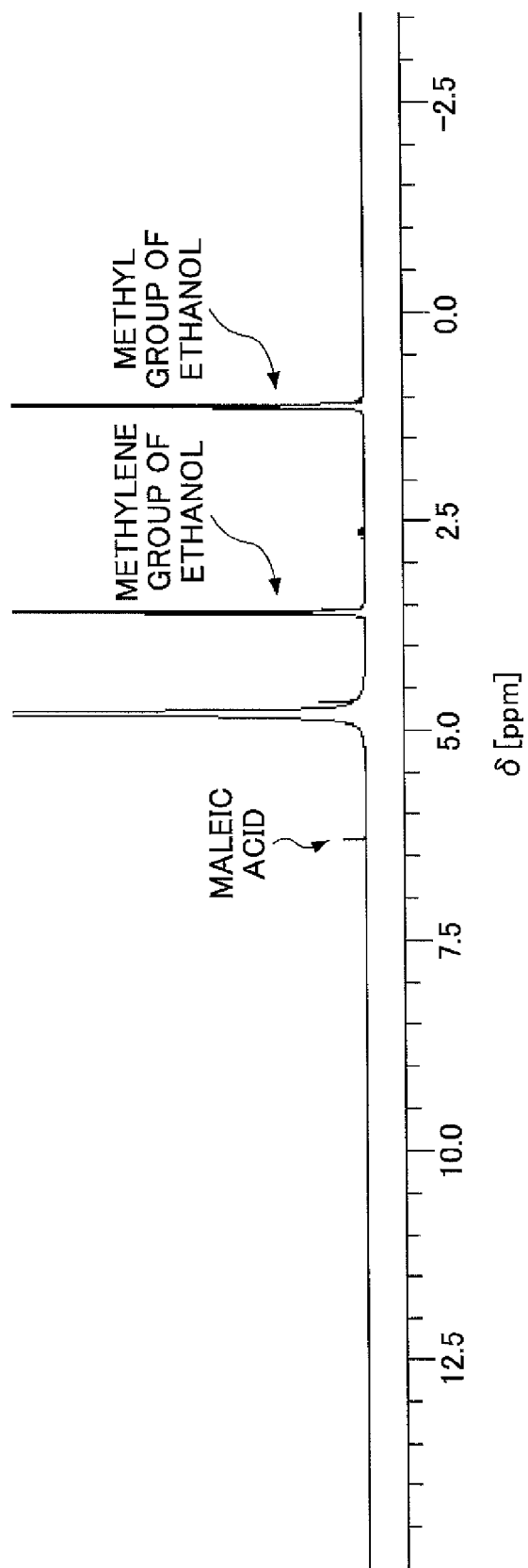

REFERENCE MATERIAL FOR NMR, SAMPLE TUBE FOR NMR, CAPILLARY FOR NMR, AND METHOD FOR MEASURING NMR FOR A SAMPLE

TECHNICAL FIELD

An aspect of the present invention relates to at least one of a reference material for NMR, a sample tube for NMR, a capillary for NMR, and a method for measuring NMR for a sample.

BACKGROUND ART

While HPLC, GC, or the like has been known as a method for quantitatively analyzing a sample conventionally, NMR is also being used.

For a method for quantifying a compound containing an oxygen-17 nucleus, Japanese Patent Application Publication No. 2004-286712 (patent document 1) discloses a method for NMR-measuring a reference material and a sample similarly, using as a reference material a substance with a resonance frequency of oxygen-17 nucleus which is different from that of a sample. Furthermore, a method for conducting measurement using a coaxial double sample tube is disclosed in which a sample and a reference material are put into an inner tube and an outer tube, respectively.

However, there may be a problem that it is not possible to ensure a quantitative capability of NMR, unless a substance with a resonance frequency of oxygen-17 nucleus which is different from that of a sample is selected for a reference material for each sample.

Furthermore, there may be a problem that whenever samples are replaced, reference materials have to be replaced accordingly, and additionally, it is not possible to conduct quantification by using a volatile reference material.

PRIOR ART DOCUMENTS

Patent Documents

Patent document 1: Japanese Patent Application Publication No. 2004-286712

SUMMARY OF THE INVENTION

Means for Solving the Problem

According to one aspect of the present invention, there is provided a reference material for NMR, including a nitrogen-containing compound or oxygen-containing compound and a reagent for shifting a chemical shift for the nitrogen-containing compound or oxygen-containing compound.

According to another aspect of the present invention, there is provided a sample tube for NMR, being obtainable by providing a reference material for NMR to a first tube closed at one end, providing a second tube closed at one end into the first tube, and fusing the other end of the first tube and the other end of the second tube and sealing a gap between the other end of the first tube and the other end of the second tube.

According to another aspect of the present invention, there is provided a sample tube for NMR, being obtainable by providing the reference material for NMR as described above to a first tube closed at one end, providing a second tube closed at one end into the first tube, and fusing the other end of the first tube and the other end of the second tube and sealing a gap between the other end of the first tube and the other end of the second tube.

According to another aspect of the present invention, there is provided a capillary for NMR, being obtainable by providing the reference material for NMR as described above to a capillary closed at one end, and fusing the other end of the capillary and closing the other end of the capillary.

According to another aspect of the present invention, there is provided a method for measuring NMR for a sample by using a reference material, wherein the reference material is the reference material for NMR as described above.

According to another aspect of the present invention, there is provided a method for measuring NMR for a sample by using a sample tube for NMR, wherein the sample tube for NMR is the sample tube for NMR as described above.

According to another aspect of the present invention, there is provided a method for measuring NMR for a sample by using a sample tube for NMR, wherein the sample tube for NMR includes the capillary for NMR as described above and the sample.

BRIEF DESCRIPTION OF THE DRAWINGS

FIG. 6 is a $^1$H-NMR spectrum for a disinfectant liquid obtained in practical example 2.

EXPLANATION OF LETTERS OR NUMERALS

Figure 1:
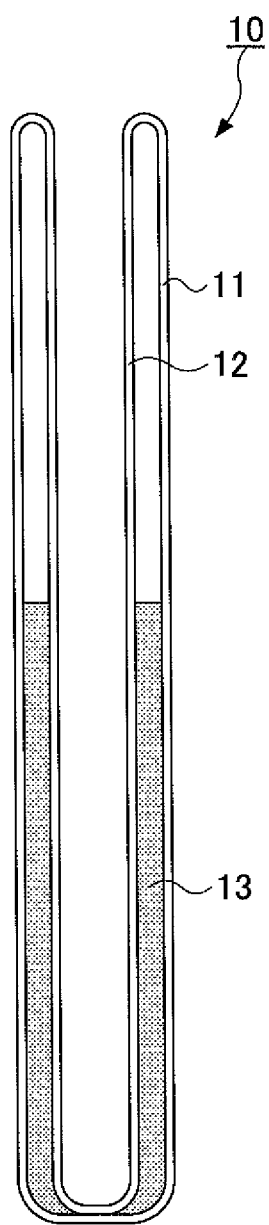
FIG. 1 is a diagram illustrating one example of an NMR sample tube according to a first embodiment of the present invention.

10 NMR sample tube
11 Outer tube
12 Inner tube
13 External reference material (FIG. 1)/Reference material (FIG. 5)
20, 20' Capillary containing an external reference material
21 Capillary
22 External reference material
23 Spacer
24 Thread

EMBODIMENTS FOR IMPLEMENTING THE INVENTION

Next, a first embodiment of the present invention will be described in conjunction with the drawings.

An external reference material for $^1$H-NMR according to a first embodiment of the present invention includes a nitrogen-containing compound or oxygen-containing compound and a shift reagent.

For a shift reagent, there is provided, for example, a lanthanide ion such as an europium ion, a praseodymium, a dysprosium ion, a ytterbium ion, a gadolinium ion, a holmium ion, or a lanthanum ion. An europium ion and a ytterbium ion allow a chemical shift of $^1$H-NMR for a compound to move to a side of a lower magnetic field and a praseodymium ion and a dysprosium ion allow a chemical shift of $^1$H-NMR for a compound to move to a side of a higher magnetic field.

In general, a shift reagent forms a complex together with a nitrogen-containing compound or oxygen-containing compound such as a nitrile, an amine, an N-oxide, an alcohol, an ether, an aldehyde, a ketone, an ester, a carboxylic acid, or an epoxide, and allows a chemical shift for a nitrogen-containing compound or oxygen-containing compound to be changed.

A nitrogen-containing compound or oxygen-containing compound is not particularly limited, and there is provided, for example, triazine, benzenetricarboxylic acid, phenazine, quinoline, trimethylamine, ethylenediamine, trimethylsilylethanesulfonamide, (trimethylsilyl)methyl alcohol, trimethylsilylmethylamine, acetone, acetylacetone, 1,3-diphenyl-1,3-propanedione, dipivaloylmethane, heptafluorodimethyloctanedione, decafluoroheptanedione, diacetyl, alanine, styreneoxide, ethylene glycol, or the like.

In general, a chemical shift of $^1$H-NMR for a compound is often present at 0-9.5 ppm. On the other hand, when a shift reagent is used, it may be possible to move a chemical shift of $^1$H-NMR for a compound to a side of a lower magnetic field or a side of a higher magnetic field with respect to 0-9.5 ppm. Herein, it may be possible for an external reference material for $^1$H-NMR according to a first embodiment of the present invention to move a chemical shift of $^1$H-NMR to a side of a lower magnetic field or a side of a higher magnetic field with respect to 0-9.5 ppm. As a result, when $^1$H-NMR is measured on a condition that an external reference material for $^1$H-NMR according to a first embodiment of the present invention is not mixed with but is separated from a sample in an NMR sample tube, a shift reagent does not act on a sample, and hence, it may be possible to completely separate a peak originating from an external reference material for $^1$H-NMR according to a first embodiment of the present invention from a peak originating from a sample.

In order to move a chemical shift of $^1$H-NMR for an external reference material for $^1$H-NMR according to a first embodiment of the present invention to a side of a magnetic field lower than 9.5 ppm, it is preferable to mix, for example, triazine and europium (III) thereto.

A chemical shift of $^1$H-NMR for triazine in deuterated chloroform is present at 9.0 ppm, and hence, when $^1$H-NMR is measured by using triazine as an external reference material, a peak of $^1$H-NMR spectrum for triazine may overlap with a peak for a sample. On the other hand, when europium (III) is added to triazine, it may be possible to move a chemical shift of $^1$H-NMR for triazine to 9.5-12 ppm. Herein, a chemical shift of $^1$H-NMR for a compound is usually present at 0.5-9.5 ppm, and hence, it may be possible to ensure a quantitative capability of $^1$H-NMR without selecting an external reference material for $^1$H-NMR according to a first embodiment of the present invention for each sample.

Herein, an equivalent ratio of europium (III) to triazine is preferably greater than or equal to 0.02, and more preferably, 0.02-0.1. If an equivalent ratio of europium (III) to triazine is less than 0.02, a chemical shift of $^1$H-NMR for triazine may not move to a side of a magnetic field lower than 9.5 ppm. Also, if an equivalent ratio of europium (III) to triazine is greater than 0.1, a line width of a signal may be broadened so that it may not be possible to obtain an accurate surface area of a peak originating from triazine.

On the other hand, in order to move a chemical shift of $^1$H-NMR for an external reference material for $^1$H-NMR according to a first embodiment of the present invention to a side of a magnetic field higher than 0 ppm, it is preferable to mix, for example, trimethylsilylethanesulfonamide and praseodymium (III) thereto.

A chemical shift of $^1$H-NMR for trimethylsilylethanesulfonamide in deuterated chloroform is present at 0.06 ppm, and hence, when $^1$H-NMR is measured by using trimethylsilylethanesulfonamide as an external reference material, a peak of $^1$H-NMR spectrum for trimethylsilylethanesulfonamide may overlap with a peak for a sample. When praseodymium (III) is added thereto, it may be possible to move a chemical shift of $^1$H-NMR for trimethylsilylethanesulfonamide to −2-0 ppm. Herein, a chemical shift of $^1$H-NMR for a compound is usually present at 0-9.5 ppm, and hence, it may be possible to ensure a quantitative capability of $^1$H-NMR without selecting an external reference material for $^1$H-NMR according to a first embodiment of the present invention for each sample.

Herein, an equivalent ratio of praseodymium (III) to trimethylsilylethanesulfonamide is preferably greater than or equal to 0.1. If an equivalent ratio of praseodymium (III) to trimethylsilylethanesulfonamide is less than 0.1, a chemical shift of $^1$H-NMR for trimethylsilylethanesulfonamide may not move to a side of a magnetic field higher than 0 ppm.

Europium (III) and praseodymium (III) are not particularly limited, and there are provided, for example, trifluoromethylhydroxymethylene-d-camphorato complexes, heptafluoropropyl-hydroxymethylene-d-camphorato complexes, D,D-dicamphoryl methanate complexes, heptafluorodimethyloctanedionate complexes, dipivaloylmethane complexes, tetramethylheptanedione complexes, or decafluoroheptanedione complexes of europium (III) and praseodymium (III), or the like.

FIG. 1 illustrates one example of an NMR sample tube according to a first embodiment of the present invention. An NMR sample tube 10 has a coaxial cylindrical double tube structure, wherein an outer tube 11 and an inner tube 12 are fusion-closed therebetween and an external reference material 13 dissolved in a deuterated solvent is put in between the outer tube 11 and the inner tube 12. Herein, the external reference material 13 is an external reference material for $^1$H-NMR according to a first embodiment of the present invention.

A deuterated solvent is not particularly limited as long as it is possible to dissolve the external reference material 13, and there is provided, for example, deuterated chloroform, deuterated acetonitrile, deuterated acetone, deuterated benzene, deuterated cyclohexane, heavy water, deuterated dichlorobenzene, deuterated diethyl ether, deuterated dimethylformamide, deuterated dimethyl sulfoxide, deuterated dioxane, deuterated ethyl acetate, deuterated ethanol, deuterated methanol, deuterated nitrobenzene, deuterated pyridine, deuterated tetrachloroethane, deuterated toluene, deuterated trifluoroacetic acid, or the like.

A length of the NMR sample tube 10 is usually 140-220 mm.

Materials for constituting the outer tube 11 and inner tube 12 are not particularly limited as long as no adverse effect is caused at time of measuring of $^1$H-NMR, and there is provided, for example, a glass, a polypropylene, a polyethylene, a polyethylene terephthalate, a polyether ether ketone, a polyvinyl chloride, a polytetrafluoroethylene, or the like.

A thickness of the outer tube 11 is usually 0.1-0.4 mm.

A thickness of the inner tuber 12 is usually 0.1-0.4 mm.

An inner diameter of the inner tube 12 is usually 1-9.5 mm.

A difference between an inner diameter of the outer tube 11 and an outer diameter of the inner tube 12 is usually 0.1-8.2 mm.

An amount of the external reference material 13 put in between the outer tube 11 and the inner tube 12 is not particularly limited as long as no adverse effect is caused at time of measuring of $^1$H-NMR.

Additionally, it may be possible to manufacture the NMR sample tube 10 by putting the external reference material 13 into a tube closed at one end, subsequently arranging a tube closed at one end therein so as to be coaxial, and conducting fusion-closure between the former tube and the latter tube. Herein, when a top of the inner tube 12 is fusion-closed so as to extend uniformly and contact the outer tube 11, a quantitative capability thereof may be improved.

Next, a method for quantitatively analyzing a sample by measuring $^1$H-NMR will be described.

First, a factor for the NMR sample tube 10 is obtained. Specifically, after a predetermined amount of a reference material for factor with a known purity dissolved in a deuterated solvent is put into the inner tube 12 and an attachable and detachable plug is provided, $^1$H-NMR is measured. Herein, when a concentration of a reference material for factor put in the inner tube 12 is $A_0$ [mol/L] and a surface area corresponding to 1H of a reference material for factor is $B_0$ in a case where a surface area of the external reference material 13 in a $^1$H-NMR spectrum is 1, F [mol/L] is represented by a formula of:

$$F = A_0/B_0 \quad (1).$$

A reference material for factor is not particularly limited, and there is provided, for example, potassium hydrogen phthalate, ethanol, or the like.

Herein, a peak of $^1$H-NMR spectrum for the external reference material 13 may be present at a side of a magnetic field lower than 9.5 ppm, and accordingly, does not overlap with a peak of $^1$H-NMR spectrum for a reference material for factor, whereby it is possible to ensure a quantitative capability of $^1$H-NMR.

Then, a content of a compound X (molecular weight M) in a sample is obtained. Specifically, after a predetermined amount of a sample dissolved in a deuterated solvent is put into the inner tube 12 and an attachable and detachable plug is provided, $^1$H-NMR is measured. Additionally, when a sample is a liquid, it may be possible to use it directly without being dissolved in a deuterated solvent. Herein, when a concentration of a sample put in the inner tube 12 is $A_1$ [g/L] and a surface area corresponding to 1H of a compound X is $B_1$ in a case where a surface area of the external reference material 13 in a $^1$H-NMR spectrum is 1, a concentration $C_1$ [g/L] of a compound X put in the inner tube 12 is represented by a formula of:

$$C_1 = B_1 \times F \times M \quad (2).$$

Therefore, a content $D_1$ [mass %] of a compound X in a sample is represented by:

$$D_1 = (C_1/A_1) \times 100 \quad (3).$$

Herein, a peak of $^1$H-NMR spectrum for the external reference material 13 may be present at a side of a magnetic field lower than 9.5 ppm, and accordingly, does not overlap with a peak of NMR spectrum for a sample, whereby it may be possible to ensure a quantitative capability of $^1$H-NMR.

Additionally, an amount of a component which is other than a compound X and is contained in a sample may also be obtained simultaneously.

Furthermore, when $^1$H-NMR for a sample is measured by using the external reference material 13, the NMR sample tube 10 may be used (see, for example, Japanese Patent Application Publication No. H01-302148) in which the outer tube 11 and the inner tube 12 are not fusion-closed therebetween and it is possible to fix the inner tube 12 in the outer tube 11. Herein, the external reference material 13 may be put into either of the outer tube 11 and the inner tube 12 or the inner tube 12 may be fusion-closed.

Figure 2:
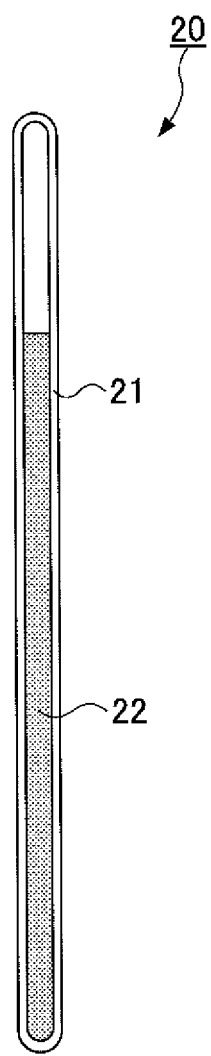
FIG. 2 is a diagram illustrating one example of a capillary containing an external reference material for $^1$H-NMR according to a first embodiment of the present invention.

FIG. 2 illustrates one example of a capillary containing an external reference material for $^1$H-NMR according to a first embodiment of the present invention. For a capillary 20 containing an external reference material, an external reference material 22 dissolved in a deuterated solvent is put in a fusion-closed capillary 21. Additionally, the external reference material 22 is an external reference material for $^1$H-NMR according to a first embodiment of the present invention.

A material for constituting the capillary 21 is not particularly limited as long as no adverse effect is caused at time of measuring of $^1$H-NMR, and there is provided, for example, a glass, a polypropylene, a polyethylene, a polyethylene terephthalate, a polyether ether ketone, a polyvinyl chloride, a polytetrafluoroethylene, or the like.

A length of the capillary 21 is usually 25-220 mm.

A thickness of the capillary 21 is usually 0.1-0.4 mm.

An inner diameter of the capillary 21 is usually 0.5-9.5 mm.

An amount of the external reference material 22 put into the capillary 21 is not particularly limited as long as no adverse effect is caused at time of measuring of $^1$H-NMR.

Additionally, it is possible to manufacture the capillary 20 containing an external reference material by putting the external reference material 22 into a capillary closed at one end and subsequently fusion-closing the capillary.

Figure 3:
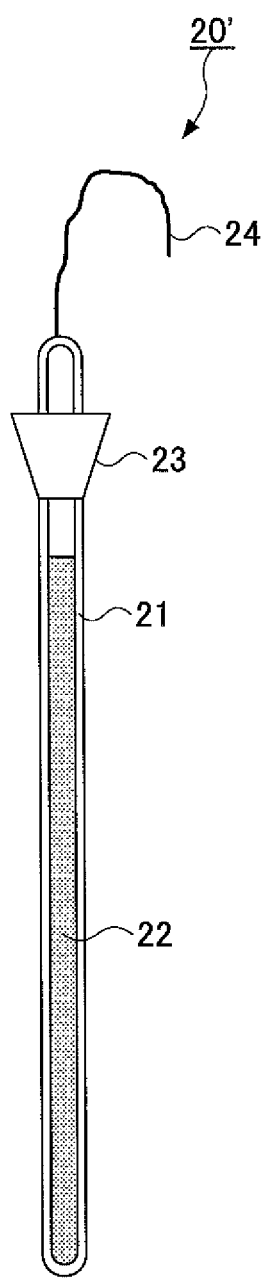
FIG. 3 is a diagram illustrating an example of variation of the capillary containing an external reference material for $^1$H-NMR in FIG. 2.

Furthermore, when a spacer 23 is attached to the capillary 21 and arranged such that a capillary 20' containing an external reference material is coaxial with an NMR sample tube, as illustrated in FIG. 3, its quantitative capability is improved. Herein, a thread 24 is attached to a top of the capillary 21, and accordingly, it may be possible to remove the capillary 20' containing an external reference material from an NMR sample tube easily. Additionally, the thread 24 may be attached to the spacer 23.

Next, a method for quantitatively analyzing a sample by measuring $^1$H-NMR will be described.

First, a factor F for the capillary 20 containing an external reference material is obtained. Specifically, after the capillary 20 containing an external reference material and a predetermined amount of a reference material for factor with a known purity dissolved in a deuterated solvent are put into an NMR sample tube and an attachable and detachable plug is provided, $^1$H-NMR is measured. Herein, when a concentration of a reference material for factor put in an NMR sample tube is $A_0$ [mol/L] and a surface area corresponding to 1H of a reference material for factor is $B_0$ in a case where a surface area of the external reference material 22 in a $^1$H-NMR spectrum is 1, F [mol/L] is represented by a formula of:

$$F = A_0/B_0 \quad (1).$$

A reference material for factor is not particularly limited, and there is provided potassium hydrogen phthalate, ethanol, or the like.

Herein, a peak of $^1$H-NMR spectrum for the external reference material 22 may be present at a side of a magnetic field lower than 9.5 ppm, and accordingly, does not overlap with a peak of $^1$H-NMR spectrum for a reference material for factor, whereby it is possible to ensure a quantitative capability of $^1$H-NMR.

Then, a content of a compound X (molecular weight M) in a sample is obtained. Specifically, after the capillary 20 containing an external reference material and a predetermined amount of a sample dissolved in a deuterated solvent is put into an NMR sample tube and an attachable and detachable plug is provided, $^1$H-NMR is measured. Additionally, when a sample is a liquid, it may be possible to use it directly without being dissolved in a deuterated solvent. Herein, when a concentration of a sample put in an NMR sample tube is $A_1$ [g/L] and a surface area corresponding to 1H of a compound X is $B_1$ in a case where a surface area of the external reference material 22 in a $^1$H-NMR spectrum is 1, a concentration $C_1$ [g/L] of a compound X put in an NMR sample tube is represented by a formula of:

$$C_1 = B_1 \times F \times M \quad (2).$$

Therefore, a content $D_1$ [mass %] of a compound X in a sample is represented by:

$$D_1 = (C_1/A_1) \times 100 \quad (3).$$

Herein, a peak of $^1$H-NMR spectrum for the external reference material 22 may be present at a side of a magnetic field lower than 9.5 ppm, and accordingly, does not overlap with a peak of NMR spectrum for a sample, whereby it may be possible to ensure a quantitative capability of $^1$H-NMR.

Additionally, an amount of a component which is other than a compound X and is contained in a sample may also be obtained simultaneously.

Next, a second embodiment of the present invention will be described in conjunction with the drawings.

Figure 5:
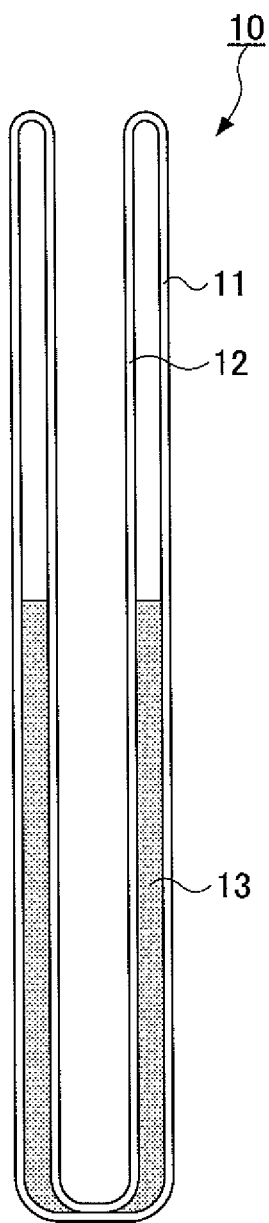
FIG. 5 is a diagram illustrating one example of an NMR sample tube according to a second embodiment of the present invention.

FIG. 5 illustrates one example of an NMR sample tube according to a second embodiment of the present invention. An NMR sample tube 10 has a coaxial cylindrical double tube structure, wherein an outer tube 11 and an inner tube 12 are fusion-closed therebetween and an external reference material 13 dissolved in a deuterated solvent is put in between the outer tube 11 and the inner tube 12. Thereby, when the NMR sample tube 10 is used, it may be possible to measure NMR not by replacing the external reference material 13 but instead by replacing a sample, and conduct its quantification even when a volatile reference material is used.

A deuterated solvent is not particularly limited as long as it is possible to dissolve the external reference material 13, and there is provided, for example, deuterated chloroform, deuterated acetonitrile, deuterated acetone, deuterated benzene, deuterated cyclohexane, heavy water, deuterated dichlorobenzene, deuterated diethyl ether, deuterated dimethylformamide, deuterated dimethyl sulfoxide, deuterated dioxane, deuterated ethyl acetate, deuterated ethanol, deuterated methanol, deuterated nitrobenzene, deuterated pyridine, deuterated tetrachloroethane, deuterated toluene, deuterated trifluoroacetic acid, or the like.

A length of the NMR sample tube 10 is usually 140-220 mm.

Materials for constituting the outer tube 11 and inner tube 12 are not particularly limited as long as no adverse effect is caused at time of measuring of NMR, and there is provided, for example, a glass, a polypropylene, a polyethylene, a polyethylene terephthalate, a polyether ether ketone, a polyvinyl chloride, a polytetrafluoroethylene, or the like.

A thickness of the outer tube 11 is usually 0.1-0.4 mm.

A thickness of the inner tuber 12 is usually 0.1-0.4 mm.

An inner diameter of the inner tube 12 is usually 1-9.5 mm.

A difference between an inner diameter of the outer tube 11 and an outer diameter of the inner tube 12 is usually 0.1-8.2 mm.

The reference material 13 is not particularly limited and there is provided, for example, a reference material for $^1$H-NMR and/or $^{13}$C-NMR such as phenazine, triazine, maleic acid, sodium 3-trimethylsilylpropionate, tetramethylsilane, sodium dimethylsilapentanesulfonate, 5-fluorouracil, benzenetricarboxylic acid, hexamethyldisiloxane, benzoquinone, formic acid, acetic acid, sodium acetate, acetic anhydride, acrylic acid, dimethyl sulfone, acetone, acetylacetone, cyclohexanone, diethyl ether, 1,1-diethoxyethane, ethyl vinyl ether, furan, tetrahydrofuran, 1,4-dioxane, dihydropyran, methanol, ethanol, isobutyl alcohol, t-butyl alcohol, ethylene glycol, 2-chloroethanol, ethyl acetate, vinyl acetate, methyl acrylate, methyl orthoformate, acetamide, dimethylformamide, trimethoxybenzene, trioxane, 1,4-bis(trimethylsilyl)benzene, 1,4-dinitrobenzene, anthracene, benzyl benzoate, biphenyl, dimethyl isophthalate, dimethylformamide, hexamethylcyclotrisiloxane, methenamine, phloroglucinol, t-butanol, tetramethylpyrazine, ethacrynic acid, dimethylfuran, chloroform, benzene, dimethyl sulfoxide, water, or acetaldehyde; a reference material for $^{19}$F-NMR such as trifluoroethanol, trifluoroacetic acid, fluorobenzene, or hexafluoroisopropanol, a reference material for $^{29}$Si-NMR such as tetramethylsilane, sodium dimethylsilapentanesulfonate, sodium 3-trimethylsilylpropionate, 1,4-bis(trimethylsilyl)benzene, trimethylsilylethanesulfonamide, trimethylsilylmethanol, or trimethylsilylamine; a reference material for $^{17}$O-NMR such as water; a reference material for $^{31}$P-NMR such as phosphoric acid, or the like. Among these, in view of a quantitative capability, a reference material for $^1$H-NMR is preferably maleic acid, tetramethylsilane, 3-trimethylsilylpropionic acid, 1,4-dioxane, 1,4-bis(trimethylsilyl)benzene, benzenetricarboxylic acid, sodium dimethylsilapentanesulfonate, triazine, phenazine, phosphoric acid, trifluoroacetic acid, water, benzene, chloroform, methanol, or dimethyl sulfoxide.

An amount of the reference material 13 put in between the outer tube 11 and the inner tube 12 is not particularly limited as long as no adverse effect is caused at time of measuring of NMR.

Additionally, it may be possible to manufacture the NMR sample tube 10 by putting the external reference material 13 into a tube closed at one end, subsequently arranging a tube closed at one end therein so as to be coaxial, and conducting fusion-closure between the former tube and the latter tube. Herein, when a top of the inner tube 12 is fusion-closed so as to extend uniformly and contact the outer tube 11, a quantitative capability thereof may be improved.

Next, a method for quantitatively analyzing a sample by measuring $^1$H-NMR will be described.

First, a factor F for the NMR sample tube 10 is obtained. Specifically, after a predetermined amount of a reference material for factor with a known purity dissolved in a deuterated solvent is put into the inner tube 12 and an attachable and detachable plug is provided, $^1$H-NMR is measured. Herein, when a concentration of a reference material for factor put in the inner tube 12 is $A_0$ [mol/L] and a surface area corresponding to 1H of a reference material for factor is $B_0$ in a case where a surface area of the reference material 13 in a $^1$H-NMR spectrum is 1, F [mol/L] is represented by a formula of:

$$F = A_0/B_0 \quad (1).$$

A reference material for factor is not particularly limited, and there is provided, for example, potassium hydrogen phthalate, ethanol, phosphoric acid, trifluoroacetic acid, sodium dimethylsilapentanesulfonate, sodium 3-trimethylsilylpropionate, water, or the like.

Additionally, in view of a quantitative capability of $^1$H-NMR, it is preferable that a peak of $^1$H-NMR spectrum for the reference material 13 used for obtaining F does not overlap with a peak of $^1$H-NMR spectrum for a reference material for factor and a peak for a reference material for factor used for obtaining F does not overlap with a peak of $^1$H-NMR spectrum for the reference material 13.

Then, a content of a compound X (molecular weight M) in a sample is obtained. Specifically, after a predetermined amount of a sample dissolved in a deuterated solvent is put into the inner tube 12 and an attachable and detachable plug is provided, $^1$H-NMR is measured. Additionally, when a sample is a liquid, it may be possible to use it directly without being dissolved in a deuterated solvent. Herein, when a concentration of a sample put in the inner tube 12 is $A_1$ [g/L] and a surface area corresponding to 1H of a compound A is $B_1$ in a case where a surface area of the reference material 13 in a $^1$H-NMR spectrum is 1, a concentration $C_1$ [g/L] of a compound X put in the inner tube 12 is represented by a formula of:

$$C_1 = B_1 \times F \times M \quad (2).$$

Therefore, a content $D_1$ [mass %] of a compound X in a sample is represented by:

$$D_1 = (C_1/A_1) \times 100 \quad (3).$$

Additionally, in view of a quantitative capability of $^1$H-NMR, it is preferable that a peak of $^1$H-NMR spectrum for the reference material 13 used for obtaining $D_1$ does not overlap with a peak of NMR spectrum for a sample and a peak of $^1$H-NMR spectrum for compound X used for obtaining $D_1$ does not overlap with any of a peak of NMR spectrum for the reference material 13 and a component which is other than compound X and is contained in a sample.

Additionally, an amount of a component which is other than a compound X and is contained in a sample may also be obtained simultaneously.

(An example(s) of embodiments of an external reference material for $^1$H-NMR and an NMR sample tube and an analysis method)

An embodiment of the present invention may relate to at least one of an external reference material for $^1$H-NMR, an NMR sample tube having a double tube structure, a capillary containing an external reference material for $^1$H-NMR, and an analysis method.

An object of an embodiment of the present invention may be to provide at least one of an external reference material for $^1$H-NMR capable of ensuring a quantitative capability of $^1$H-NMR without being selected for each sample, an NMR sample tube and capillary in which the external reference material for $^1$H-NMR is put, and an analysis method using the external reference material for $^1$H-NMR.

An object of an embodiment of the present invention may be to provide at least one of an NMR sample tube capable of measuring NMR by not replacing a reference material but replacing a sample and of conducting its quantification even when a volatile reference material is used, and an analysis method using the NMR sample tube.

Embodiment (1-1) of the present invention is an external reference material for $^1$H-NMR, characterized by including a nitrogen-containing compound or oxygen-containing compound and a shift reagent.

Embodiment (1-2) of the present invention is the external reference material for $^1$H-NMR according to embodiment (1-1) of the present invention, characterized by including triazine and europium (III).

Embodiment (1-3) of the present invention is an external reference material for $^1$H-NMR according to embodiment (1-2) of the present invention, characterized in that an equivalent ratio of the europium (III) to the triazine is greater than or equal to 0.02.

Embodiment (1-4) of the present invention is the external reference material for $^1$H-NMR according to embodiment (1-1) of the present invention, characterized by including trimethylsilylethanesulfonamide and praseodymium (III).

Embodiment (1-5) of the present invention is the external reference material for $^1$H-NMR according to embodiment (1-4) of the present invention, characterized in that an equivalent ratio of the praseodymium (III) to the trimethylsilylethanesulfonamide is greater than or equal to 0.1.

Embodiment (1-6) of the present invention is an NMR sample tube having a double tube structure, characterized in that an outer tube and an inner tune are fusion-closed therebetween and the external reference material for $^1$H-NMR according to any one of embodiments (1-1) to (1-5) of the present invention is put in between the outer tube and the inner tube.

Embodiment (1-7) of the present invention is a capillary containing an external reference material for $^1$H-NMR, characterized in that the external reference material for $^1$H-NMR according to any one of embodiments (1-1) to (1-5) of the present invention is put in a fusion-closed capillary.

Embodiment (1-8) of the present invention is an analysis method characterized by including a step of measuring $^1$H-NMR for a sample by using the external reference material for $^1$H-NMR according to any one of embodiments (1-1) to (1-5) of the present invention.

Embodiment (1-9) of the present invention is an analysis method characterized by including a step of putting a sample into an inner tube of the NMR sample tube according to embodiment (1-6) of the present invention and a step of measuring $^1$H-NMR for the sample by using the NMR sample tube in which the sample is put.

Embodiment (1-10) of the present invention is an analysis method characterized by including a step of putting the capillary containing an external reference material for $^1$H-NMR according to embodiment (1-7) of the present invention and a sample into an NMR sample tube and a step of measuring $^1$H-NMR for the sample by using the capillary containing an external reference material for $^1$H-NMR and the NMR sample tube in which a sample is put.

Embodiment (1-11) of the present invention is an analysis method according to any one of embodiments (1-8) to (1-10) of the present invention, characterized by quantitatively analyzing the sample by measuring $^1$H-NMR for the sample.

Embodiment (2-1) of the present invention is an NMR sample tube having a double tube structure, characterized in that an outer tube and an inner tube are fusion-closed therebetween and a reference material is put in between the outer tube and the inner tube.

Embodiment (2-2) of the present invention is the NMR sample tube according to embodiment (2-1) of the present invention, characterized in that the reference material is maleic acid, tetramethylsilane, 3-trimethylsilylpropionic acid, 1,4-dioxane, 1,4-bis(trimethylsilyl)benzene, benzenetricarboxylic acid, sodium dimethylsilapentanesulfonate, triazine, phenazine, phosphoric acid, trifluoroacetic acid, water, benzene, chloroform, methanol, or dimethyl sulfoxide.

Embodiment (2-3) of the present invention is an analysis method characterized by including a step of putting a sample into an inner tube of the NMR sample tube according to embodiment (2-1) or (2-2) of the present invention and a step of measuring NMR for the sample by using the NMR sample tube in which the sample is put.

Embodiment (2-4) of the present invention is the analysis method according to embodiment (2-3) of the present invention, characterized by quantitatively analyzing the sample by using the NMR.

According to an embodiment of the present invention, it may be possible to provide at least one of an external reference material for $^1$H-NMR capable of ensuring a quantitative capability of $^1$H-NMR without being selected for each sample, an NMR sample tube and capillary in which the external reference material for $^1$H-NMR is put, and an analysis method using the external reference material for $^1$H-NMR.

According to an embodiment of the present invention, it may be possible to provide at least one of an NMR sample tube capable of measuring NMR by not replacing a reference material but replacing a sample and of conducting its quantification even when a volatile reference material is used, and an analysis method using the NMR sample tube.

Practical Example 1

[Preparation of a Reference Material Solution for Factor]

200.5 mg of potassium hydrogen phthalate (molecular weight 204.2212) was weighed precisely and dissolved in heavy water so as to be 20 mL accurately, whereby 0.049089 mol/L of a reference material solution for factor was obtained.

[Evaluation of Factors]

A suitable amount of the reference material solution for factor was put into an inner tube 12 of an NMR sample tube 10 (see FIG. 1) in which an external reference material 13 dissolved in deuterated chloroform is put in between an outer tube 11 and the inner tube 12 and an attachable and detachable plug was applied thereto. Herein, the equivalent ratio of europium (III) to triazine was 0.05. Then, $^1$H-NMR was measured 6 times using ECA-400 (produced by JEOL Ltd.; 400 MHz) in the conditions of a pulse width of 5.35 microseconds, a repetition time of about 60 seconds, and a cumulated number of 16 times. $B_0$ (see Table 1) was obtained from an obtained $^1$H-NMR spectrum. Herein, 3 NMR sample tubes 1-3 were used.

TABLE 1

| | $B_0$ | | |
|---|---|---|---|
| | NMR sample tube 1 | NMR sample tube 2 | NMR sample tube 3 |
| 1st time | 0.34135 | 0.32537 | 0.34818 |
| 2nd time | 0.34025 | 0.32867 | 0.34644 |
| 3rd time | 0.34068 | 0.32786 | 0.34534 |
| 4th time | 0.34188 | 0.33119 | 0.34466 |
| 5th time | 0.34058 | 0.32806 | 0.34747 |
| 6th time | 0.34301 | 0.32780 | 0.34621 |
| Average | 0.34129 | 0.32816 | 0.34638 |
| Relative standard deviation [%] | 0.30 | 0.57 | 0.38 |

Then, factors F for NMR sample tubes 1-3 were calculated by using formula (1), and as a result, were 0.14383 [mol/L], 0.14959 [mol/L], and 0.14172 [mol/L], respectively.

[Preparation of Sample Solutions]

A food additive was weighed precisely and dissolved in deuterated chloroform so as to be accurately 2 mL, whereby sample solutions 1-3 (see Table 2) were obtained.

TABLE 2

| | Sample solution 1 | Sample solution 2 | Sample solution 3 |
|---|---|---|---|
| Amount of added food additive [mg] | 39.5 | 40.6 | 41.2 |
| $A_1$ [g/L] | 19.75 | 20.30 | 20.60 |

[Evaluation of Amounts of Methanol Remaining in Food Additives]

Figure 4:
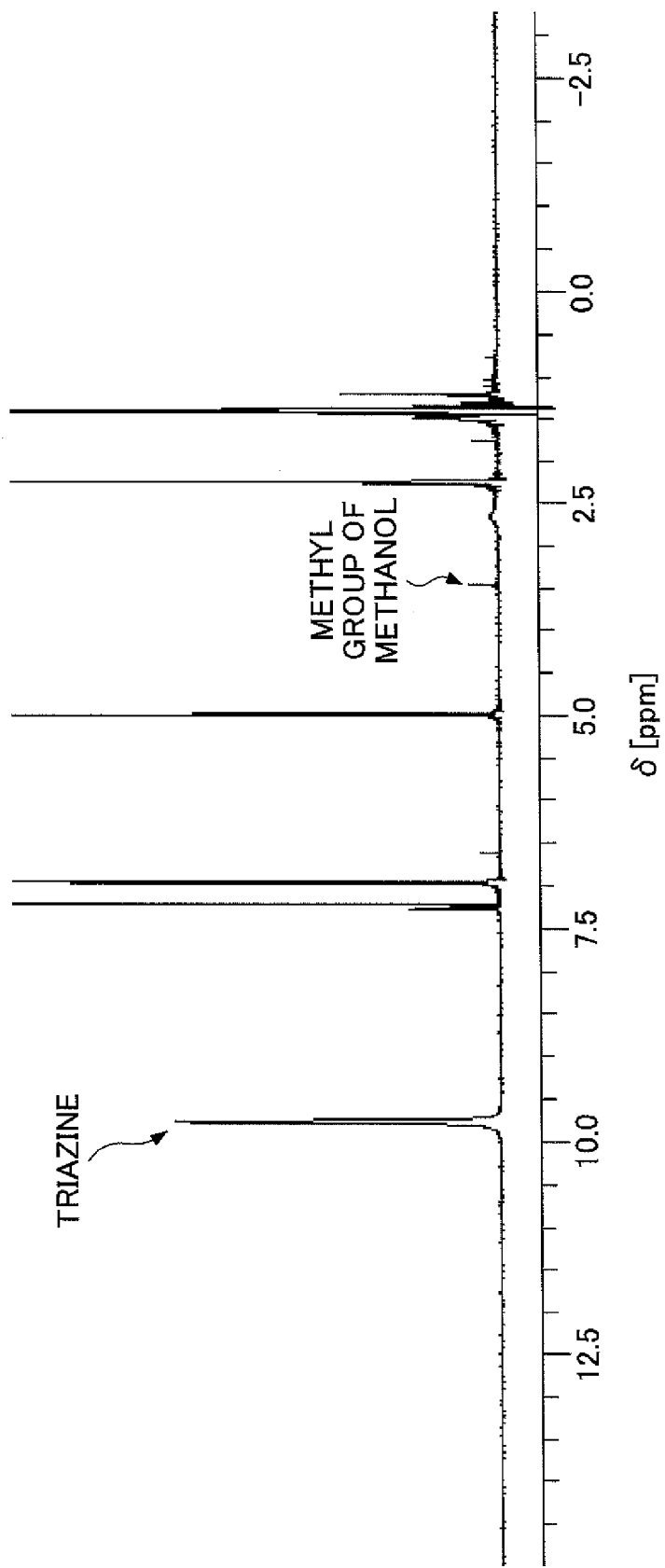
FIG. 4 is a $^1$H-NMR spectrum for a sample solution obtained in practical example 1.

Suitable amounts of samples solutions 1-3 were put into inner tubes 12 of NMR sample tubes 1-3 whose factors had been evaluated, respectively, and attachable and detachable plugs were applied thereto. Then, $^1$H-NMR was measured for each 3 times on the conditions identical to those of evaluation of the factors except that the cumulated number was changed to 64 times. $B_1$ (see Table 3) was obtained from a peak originating from a methyl group of methanol in an obtained $^1$H-NMR spectrum (see FIG. 4).

TABLE 3

| | $B_1$ | | |
|---|---|---|---|
| | Sample solution 1 | Sample solution 2 | Sample solution 3 |
| 1st time | 0.00329 | 0.00286 | 0.00315 |
| 2nd time | 0.00323 | 0.00258 | 0.00285 |
| 3rd time | 0.00310 | 0.00279 | 0.00297 |
| Average | 0.00321 | 0.00274 | 0.00299 |
| Relative standard deviation [%] | 3.03 | 5.31 | 5.05 |

Then, an amount $D_1$ (see Table 4) of methanol (molecular weight 32.04) remaining in the food additive was calculated by using formulas (2) and (3).

TABLE 4

| | $D_1$ [mass %] | | |
|---|---|---|---|
| | Sample solution 1 | Sample solution 2 | Sample solution 3 |
| 1st time | 0.0768 | 0.0675 | 0.0694 |
| 2nd time | 0.0754 | 0.0609 | 0.0628 |
| 3rd time | 0.0723 | 0.0659 | 0.0655 |
| Average | 0.0748 | 0.0648 | 0.0659 |
| Relative standard deviation [%] | 3.08 | 5.31 | 5.04 |
| Gross average | | 0.0685 | |
| Relative standard deviation [%] | | 7.98 | |

Herein, an amount of methanol remaining in the food additive was measured by means of gas chromatography, and as a result, was 0.0697 mass %. From this fact, it is found that the quantitative capability of $^1$H-NMR was ensured in the present practical example.

Practical Example 2

[Preparation of a Reference Material Solution for Factor]
200.2 mg of potassium hydrogen phthalate (molecular weight 204.2212) was weighed precisely and dissolved in heavy water so as to be 20 mL accurately, whereby 0.049015 mol/L of a reference material solution for factor was obtained.

[Evaluation of a Factor]
A suitable amount of the reference material solution for factor was put into an inner tube 12 of an NMR sample tube 10 (see FIG. 5) in which a reference material 13 (maleic acid) dissolved in heavy water was put in between an outer tube 11 and the inner tube 12 and an attachable and detachable plug was applied thereto. Then, $^1$H-NMR was measured 3 times by using ECA-400 (produced by JEOL Ltd.; 400 MHz) on the conditions of a pulse width of 5.35 microseconds, a repetition time of about 60 seconds, and a cumulated number of 16 times. $B_0$ (see Table 5) was obtained from an obtained $^1$H-NMR spectrum.

TABLE 5

|  | $B_0$ |
| --- | --- |
| 1st time | 0.22725 |
| 2nd time | 0.22638 |
| 3rd time | 0.22460 |
| Average | 0.22608 |
| Relative standard deviation [%] | 0.60 |

Then, a factor F was calculated by using formula (1), and as a result, was 0.21681[mol/L].

[Evaluation of a Concentration of Ethanol in a Disinfectant Liquid]
A suitable amount of a disinfectant liquid was put into the inner tube 12 of the NMR sample tube 10 whose factor has been evaluated, and an attachable and detachable plug was applied thereto. Then, $^1$H-NMR was measured 3 times on the conditions identical to those of evaluation of the factor. $B_1$ (see Table 6) was obtained from a peak originating from a methyl group and a peak originating from a methylene group of ethanol in an obtained $^1$H-NMR spectrum (see FIG. 6).

TABLE 6

|  | $B_1$ | |
| --- | --- | --- |
|  | Methyl group | Methylene group |
| 1st time | 24.53601 | 24.62549 |
| 2nd time | 23.82240 | 23.83774 |
| 3rd time | 24.64078 | 24.64894 |
| Average | 24.33306 | 24.37072 |
| Relative standard deviation [%] | 1.83 | 1.89 |
| Gross average | 24.35189 | |
| Relative standard deviation [%] | 1.67 | |

Then, a concentration $C_1$ of ethanol (molecular weight 46.07) put in the inner tube 12 was calculated by using formula (2), and as a result, was 243.23[g/L].

Although some embodiment(s) and practical example(s) of the present invention have been described with reference to the accompanying drawing(s), the present invention is not limited to any of such embodiment(s) and practical example(s), and such embodiment(s) and practical example(s) may be altered, modified, or combined without departing from the scope of the present invention.

The present application claims its priority based on Japanese patent application No. 2010-001200 filed on Jan. 6, 2010 and Japanese patent application No. 2010-001201 filed on Jan. 6, 2010, the entire contents of which are herein incorporated by reference.

The invention claimed is:

1. A reference material for NMR measurement, comprising triazine and europium (III) as a reagent for shifting a chemical shift for triazine,
   wherein a chemical shift of $^1$H-NMR for triazine in deuterated chloroform is moved to greater than or equal to 9.5 ppm and less than or equal to 12 ppm by the europium (III).

2. The reference material for NMR measurement as claimed in claim 1, wherein an equivalent ratio of the europium (III) to the triazine is 0.02 or greater.

3. A sample tube for NMR measurement, obtainable by providing the reference material for NMR measurement as claimed in claim 1 to a first tube closed at one end, providing a second tube closed at one end into the first tube, and fusing the other end of the first tube and the other end of the second tube to seal a gap between the other end of the first tube and the other end of the second tube.

4. A method for measuring NMR measurement for a sample by using a sample tube for NMR measurement, wherein the sample tube for NMR measurement is the sample tube for NMR measurement as claimed in claim 3.

5. A capillary for NMR measurement, obtainable by providing the reference material for NMR measurement as claimed in claim 1 to a capillary closed at one end and fusing the other end of the capillary and to close the other end of the capillary.

6. A method for measuring NMR measurement for a sample by using a sample tube for NMR measurement, wherein the sample tube for NMR measurement includes the capillary for NMR measurement as claimed in claim 5 and the sample.

7. A method for measuring NMR measurement for a sample by using a reference material, wherein the reference material is the reference material for NMR measurement as claimed in claim 1.

8. A reference material for NMR measurement comprising trimethylsilylethanesulfonamide and praseodymium (III) as a reagent for shifting a chemical shift for trimethylsilylethanesulfonamide,
   wherein a chemical shift of $^1$H-NMR for trimethylsilylethanesulfonamide in deuterated chloroform is moved to greater than or equal to −2 ppm and less than or equal to 0 ppm by the praseodymium MD.

9. The reference material for NMR measurement as claimed in claim 8, wherein an equivalent ratio of the praseodymium (III) to the trimethylsilylethanesulfonamide is 0.1 or greater.

10. A sample tube for NMR measurement, obtainable by providing the reference material for NMR measurement as claimed in claim 8 to a first tube closed at one end, providing a second tube closed at one end into the first tube, and fusing the other end of the first tube and the other end of the second tube to seal a gap between the other end of the first tube and the other end of the second tube.

11. A method for measuring NMR measurement for a sample by using a sample tube for NMR measurement, wherein the sample tube for NMR measurement is the sample tube for NMR measurement as claimed in claim 10.

12. A capillary for NMR measurement, obtainable by providing the reference material for NMR measurement as claimed in claim 8 to a capillary closed at one end, and fusing the other end of the capillary to close the other end of the capillary.

13. A method for measuring NMR measurement for a sample by using a sample tube for NMR measurement, wherein the sample tube for NMR measurement includes the capillary for NMR measurement as claimed in claim 12 and the sample.

14. A method for measuring NMR measurement for a sample by using a reference material, wherein the reference material is the reference material for NMR measurement as claimed in claim 8.

15. A sample tube for NMR measurement, obtainable by
providing a reference material for NMR measurement to a first tube closed at one end,
providing a second tube closed at one end into the first tube such that the reference material is positioned between the first tube and the second tube, and
fusing the other end of the first tube and the other end of the second tube to seal a gap between the other end of the first tube and the other end of the second tube.

16. The sample tube for NMR measurement as claimed in claim 15, wherein the reference material is selected from the group consisting of maleic acid, tetramethylsilane, 3-trimethylsilylpropionic acid, 1,4-dioxane, 1,4-bis(trimethylsilyl)benzene, benzenetricarboxylic acid, sodium dimethylsilapentaneslfonate, triazine, phenazine, phosphoric acid, trifluoroacetic acid, water, benzene, chloroform, methanol, and dimethyl sulfoxide.

17. A method for measuring NMR measurement for a sample by using a sample tube for NMR measurement, wherein the sample tube for NMR measurement is the sample tube for NMR measurement as claimed in claim 15.

* * * * *